United States Patent [19]

Lund et al.

[11] Patent Number: 5,733,750
[45] Date of Patent: Mar. 31, 1998

[54] PROCESS FOR CHEMICAL FINISHING OF INSOLUBLE POLYMERS

[75] Inventors: Henrik Lund; Ole Kirk, both of Copenhagen N., Denmark

[73] Assignee: Novo Nordisk A/S, Bagsvaerd, Denmark

[21] Appl. No.: 801,326

[22] Filed: Feb. 18, 1997

Related U.S. Application Data

[63] Continuation of Ser. No. 330,754, Oct. 28, 1994, abandoned.

[51] Int. Cl.⁶ .................. C12P 19/00; C12P 19/04; C12P 7/64; D06M 13/184
[52] U.S. Cl. .................. 435/72; 435/74; 435/101; 435/134; 435/135; 536/58; 536/107; 536/115; 536/63; 8/120
[58] Field of Search .................. 435/101, 134, 435/135, 72, 74; 536/58, 107, 115, 63; 8/120

[56] References Cited

U.S. PATENT DOCUMENTS

| | | | |
|---|---|---|---|
| 3,909,360 | 9/1975 | Horiuchi | 435/178 |
| 4,614,718 | 9/1986 | Seino et al. | 435/72 |
| 5,042,986 | 8/1991 | Kitchens et al. | 8/120 |
| 5,191,071 | 3/1993 | Kirk et al. | 536/4.1 |

FOREIGN PATENT DOCUMENTS 4012351  10/1991  Germany.

*Primary Examiner*—Leon B. Lankford, Jr.
*Assistant Examiner*—Francisco C. Prats
*Attorney, Agent, or Firm*—Steve T. Zelson, Esq.; Valeta Gregg, Esq.

[57] ABSTRACT

Disclosed is a process for chemical finishing of fabrics, fibers or yarns wherein insoluble cellulosic polymers are reacted with carboxylic acids or esters thereof in the presence of a lipase. The cellulosic polymer may be cotton, viscose, rayon, lyocell, flax, linen, ramie, and all blends thereof; and blends thereof with polyesters, wool, polyamides, acrylics and polyacrylics. The lipase may be a microbial lipase, including a lipase obtained from yeast, e.g. Candida lipase, a bacterial lipase, e.g. Pseudomonas lipase, or a fungal lipase, e.g. Humicola or Rhizomucor lipases. Chemically modified lipases obtained by coupling polyethylene glycol to amino acid residues of the lipase may also be used.

9 Claims, No Drawings

PROCESS FOR CHEMICAL FINISHING OF INSOLUBLE POLYMERS

This application is a continuation of application Ser. No. 08/330,754 filed Oct. 28, 1994 now abandoned, the contents of which are fully incorporated herein by reference.

The present invention relates to a process for chemical finishing of insoluble polymers. More specifically, the invention relates to an enzymatic esterification of insoluble polymers wherein organic molecules containing a carboxylic acid residue are covalently linked to insoluble polymers such as cellulosic fibres or textile fabric, the fibre or fabric made therefrom having improved functional properties such as reduced tendency to wrinkling, improved durable softness, anti-static appearance, water repellency, enchanced soil release or flame retardancy.

BACKGROUND OF THE INVENTION

In chemical finishing of textile fabrics two traditional ways of processing have been to either deposit materials onto the fabric or to react a material with the fabric. An example of the former is the application of softener finishes which may improve the hand and drape of fabrics, add body to the fabric, facilitate application of other finishes and increase the life and utility of the fabric. Softeners are usually available in three types: nonionic, anionic and cationic. As groups the anionic and nonionic softeners usually serve more as lubricants rather than softeners, while the cationic softeners are probably the best softening agents available. The cationic softeners impart a soft, silky and bulky hand in the fabric. The most common type of cationic softeners are the quaternary ammonium salts which have affinity for most textile fibers, as due to their positive charge. Since most fibers develop a negative surface charge in water, the cationic softeners exhaust onto the fibers.

In recent years there has, however, been an increasing enviromental concern about the usage of the quaternary ammonium salts as due to thein low bio-degradability as well as their fairly high toxicity.

Lipases and esterases are well known as catalysts capable of catalyzing synthesis of esters by reacting an alcohol with either a carboxylic acid or an ester thereof solubilized in an organic solvent with low water-activity. Furthermore, these catalysts have proven efficient for esterification of various carbohydrates solubilized in organic solvents. Even though suspension of free enzymes have shown some effect immobilized enzymes have preferably been used as they exhibit improved stability in the organic solvents and, furthermore, offer obvious benefits regarding re-use of the catalyst. One example is the esterification of simple alkyl glucosides catalyzed by immobilized lipases in organic solvents with low water activity described in U.S. Pat. No. 5,191,071.

Recently, various methods have been developed for solubilizing enzyme catalysts in organic media by either chemical modification of the enzyme with organic polymers such as PEG (K. Takahashi et al. Biochem. Biophys. Re. Commun. 1984, 121, 261 and T. Yoshimoto et al. Biotech Lett. 1984, 6, 337 and K. Takahashi et al. J. Org. Chem. 1985, 50, 3414) or by complexing the catalyst with organic polymers (Y. Okahata and K. Ijiro, Bull. Chem. Jpn. 1992, 65, 2411). These methods have enabled reaction between solubilized organic substrates and soluble enzyme catalysts.

As described above, both immobilized and solubilized enzymes have been shown to be efficient for catalyzing esterification reactions by combining various solubilized substrates (including simple carbohydrates) in a suitable organic solvent with low water activity. However, no esterification of insoluble substrates has, so far, been described in the prior art.

Surprisingly, it has been found that hydrolyric enzymes such as lipases and esterases are capable of catalyzing esterification of insoluble substrates such as cellulose.

SUMMARY OF THE INVENTION

Surprisingly, it has been found that it is possible to carry out chemical finishing of textiles, fibres, yarns etc. containing insoluble polymers, especially cellulose, by an enzymatic process in which a hydrolyric enzyme such as a lipase or an esterase catalyzes the formation of ester bonds between the polymer and a suitable reactant containing one or more carboxy functions.

Accordingly, the present invention provides a process for enzymatically catalyzing an esterification of insoluble polymers containing free hydroxy groups, wherein the polymer is reacted with a carboxylic acid or an ester thereof in the presence of an enzyme capable of catalyzing esterfication.

Chemical finishing of textiles, fibres and yarns serves to improve the properties of the resulting product, usually a textile e.g. for garments, carpeting, upholstery. Examples of such properties are permanent press, softening, soil release, water repellancy and flame retardancy. The present invention provides a process by which, in dependance of the chemical substance actually attached to the polymer by an ester bond, one or more of the desired properties may be obtained or improved in an easy, economical and environmental-friendly way.

Further, the process of the invention provides a durable finishing of the polymer, i.e. provides a permenent improvement to the polymer, in contrast to deposition finishings wherein a chemical substance is deposited on the polymer and, thus, may be easily removed mechanically when laundering or wearing or otherwise using the polymeric material.

DETAILED DESCRIPTION OF THE INVENTION

The polymeric substrate

In the present specification and claims, the term "insoluble polymer containing free hydroxy groups" is intended to mean a polymeric material having hydroxy groups capable of forming ester bonds when contacted with carboxy groups, i.e. carboxylic acids or esters thereof.

Preferably, the polymeric material subjected to the process of the invention is present as a fiber, a staple fiber such as a solvent-spun fiber, a filament, a thread, a film, a yarn, or a textile fabric which may be woven, nonwoven or knitted.

In a preferred embodiment of the invention, the polymer is a cellulosic polymer, i.e. containing cellulose or cellulose derivatives, preferably a polymer selected from the group consisting of cotton, viscose (rayon), lyocell, flax (linen), ramie, and all blends thereof; and blends thereof with polyesters, wool, polyamides and (poly)acrylics. Typical examples of such blends are viscose/cotton, viscose/polyester, lyocell/polyester, lyocell/cotton, cotton/acrylic, cotton/polyester, cotton/polyester/acrylic, cotton/polyamide/polyester.

In another preferred embodiment of the invention, the polymer is synthetic polymer. Preferably, the synthetic polymer is selected from the group consisting of polyesters, polyamides, nylons, (poly)acrylics.

The carboxylic acid

In the present specification and claims, the term "carboxylic acid or an ester thereof" is intended to mean any carboxylic acid or ester which improves one or more properties of the polymeric material and is capable of forming ester bonds with the free hydroxy groups of the polymer.

It is contemplated that, e.g. for obtaining an improvement of the softening finish, i.e. improvement of the hand and drape of the final fabric, for obtaining flame retardancy, for obtaining water repellancy and for obtaining resin finishing ("permanent press"), it may be convenient to use in the process of this invention a carboxylic acid or an ester thereof with the general formula (I)

R—COOR¹                                         (I)

wherein

R is a linear or branched $C_{1-25}$ alkyl chain which optionally is substituted with one or more carboxy, nitro, chloro, bromo, fluoro, amino, hydroxy, keto; and $R^1$ is hydrogen, $C_{1-4}$ alkyl, or vinyl, preferably methyl, ethyl or vinyl.

For obtaining permanent press, it is advantageous to use a poly-carboxylic acid or an ester thereof, i.e. a carboxylic acid with two or more carboxy groups capable of forming ester bonds.

For obtaining flame retardancy, it is advantageous to use a halogen-substituted carboxylic acid or an ester thereof, i.e. a fluorinated, chlorinated or bromated carboxylic acid or an ester thereof.

Further, it is contemplated that the process of the invention is useful for dyeing the polymeric material by reacting the polymeric material with an carboxylic acid or ester thereof of the general formula (I)

R—COOR¹                                         (I)

wherein R comprises a chromophore. Usually, the chromophore comprises one or more heterocycles, preferably comprising one or more nitrogen, sulphur or oxygen atoms. Examples of useful chromophores are derivatives of acridines and phenazines.

Further, it is contemplated that the process of the invention is useful for obtaining brightness, e.g. optical brightness, of the polymeric material by reacting the polymeric material with an carboxylic acid or ester thereof of the general formula (I)

R—COOR¹                                         (I)

wherein R comprises a fluorophore. Examples of useful fluorophores are derivatives of xanthenes.

Further, it is contemplated that the process of the invention is useful for obtaining water repellancy of the polymeric material by reacting the polymeric material with a wax or a derivative of a wax containing one or more carboxy groups capable of forming ester bonds.

The enzyme

In the present specification and claims, the terms "lipase" and "esterase" are intended to mean an enzyme that in an aqueous environment hydrolyses ester linkages present in either water-soluble molecules or water in-soluble molecules (e.g. long chain lipide).

The lipase is suitably a microbial lipase. As such, the parent lipase may be selected from yeast, e.g. Candida lipases, bacterial, e.g. Pseudomonas lipases or fungal, e.g. Humicola or Rhizomucor lipases. More specifically, suitable lipases may be the *Rhizomucor miehei* lipase (e.g. prepared as described in EP 238 023), *Humicola lanuginosa* lipase e.g. prepared as described in EP 305 216 (available from Novo Nordisk under the trade name Lipolase™), *Candida antarctica* lipase A or B, or *Pseudomonas cepacia* lipase. Other examples of suitable lipases are variants of any one of the lipases mentioned above, e.g. as described in WO 92/05249 or WO 93/11254.

A useful esterase is suitably of microbial origin. As such the esterase may be either fungal, bacterial or from yeast.

Other useful enzymes are chemically modified lipases or esterases which may be obtained by the coupling of a polyethyleneglycol (PEG) to amino acid residues in the lipase as described in K. Takahashi et al. Biochem. Biophys. Re. Commun. 1984, 121, 261 and T. Yoshimoto et al. Biotech Lett. 1984, 6, 337 and K. Takahashi et al. J. Org. Chem. 1985, 50, 3414; or by complexing the lipase with organic polymers as described in Y. Okahata and K. Ijiro, Bull. Chem. Jpn., 1992, 65, 2411.

Process conditions

It is obvious to the skilled person that the process must be carried out under conditions (e.g. temperature, pH, solvent) which favours the esterification process over the undesired hydrolyric cleavage of ester bonds. Accordingly, it is impossible to carry out the desired esterification process when using water as a solvent.

The process of the invention may be carried out in a suitable solvent. Preferably, the solvent is an organic solvent of low water-activity, preferably a water activity below 50%. It is contemplated that conventional organic solvents except alcohols are useful in the process of the invention.

However, when the carboxylic acid or the ester to be used is liquid at the process temperature, the process may be carried out without a solvent.

Alternatively, the reaction may take place in a microemulsion formed by adding an carboxylic acid or an ester thereof to a mixture of water and a suitable surfactant. Typically, the surfactant is a nonionic surfactant.

The following non-limiting example illustrates the invention.

EXAMPLE

A cotton swatch (2×2 cm) was added to a solution of decanoic acid (50 mg) in butanone (10 ml). Lipase from *Candida antarctica* (available from Novo Nordisk A/S) was then added and the mixture was vigorously stirred at 50° C. for 24 hours. The swatch was then rinsed thoroughly in butanone (3×10 ml) and dried at room temperature for 2 hours. The swatch was then treated with an aqueous solution (5 ml) of sodium hydroxide (1M) at 40° C. for 1 hour. The swatch was removed and the solution was then acidified with hydrochloric acid to a pH of 2. Extraction of this solution with chloroform (5 ml) afforded an extract which was evaporated in vacuo. Analysis by NMR spectroscopy (employing a Bruker acp 300 NMR spectrometer and using deuterated chloroform as solvent) indicated the extract to contain decanoic acid.

Another swatch was treated as above, only adding no enzyme to the butanone. NMR analysis failed to prove any presence of decanoic acid in the final chloroform extract.

Accordingly, this example shows that the first swatch had been successfully esterified with decanoic acid in the presence of lipase as the catalyst.

We claim:

1. A process for chemical finishing of: fabrics, fibers, or yarns containing insoluble cellulosic polymer, the cellulosic polymer also containing free hydroxy groups, the process comprising the steps of:

(a) reacting the cellulosic polymer with a carboxylic acid or an ester thereof, (b) catalyzing the process with a lipase or other esterase capable of esterification of the cellulosic polymers.

2. The process according to claim 1, wherein the cellulosic polymer is selected from the group consisting of cotton, viscose, rayon, lyocell, flax, linen, ramie, and all blends thereof; and blends thereof with polyesters, wool, polyamide, acrylics and polyacrylics.

3. The process according to claim 1, wherein the carboxylic acid or the ester thereof has the general formula (I)

R—COOR$^1$ wherein R is a linear or branched $C_{1-25}$ alkyl chain and $R^1$ is hydrogen, $C_{1-14}$ alkyl, or vinyl.

4. The process of claim 3, wherein the alkyl chain is substituted with one or more of carboxyl, nitro, chloro, bromo, fluoro, amino, hydroxy or keto; and $R^1$ is hydrogen, $C^{1-4}$ alkyl, or vinyl.

5. The process according to claim 1, wherein the carboxylic acid or the ester thereof has the general formula (I)

R—COOR$^1$ wherein R comprises a chromophore or a fluorophore and $R^1$ is hydrogen, $C_{1-4}$ alkyl, or vinyl.

6. The process according to claim 1, wherein the carboxylic acid or the ester thereof is a wax.

7. The process according to claim 1, wherein the lipase is a microbial lipase.

8. The process according to claim 7, wherein the microbial lipase is a chemically modified lipase obtained by the coupling of a polyethyleneglycol to amino acid residues in the lipase.

9. The process of claim 1 wherein the cellulosic polymer is water insoluble.

* * * * *